Figure 1:
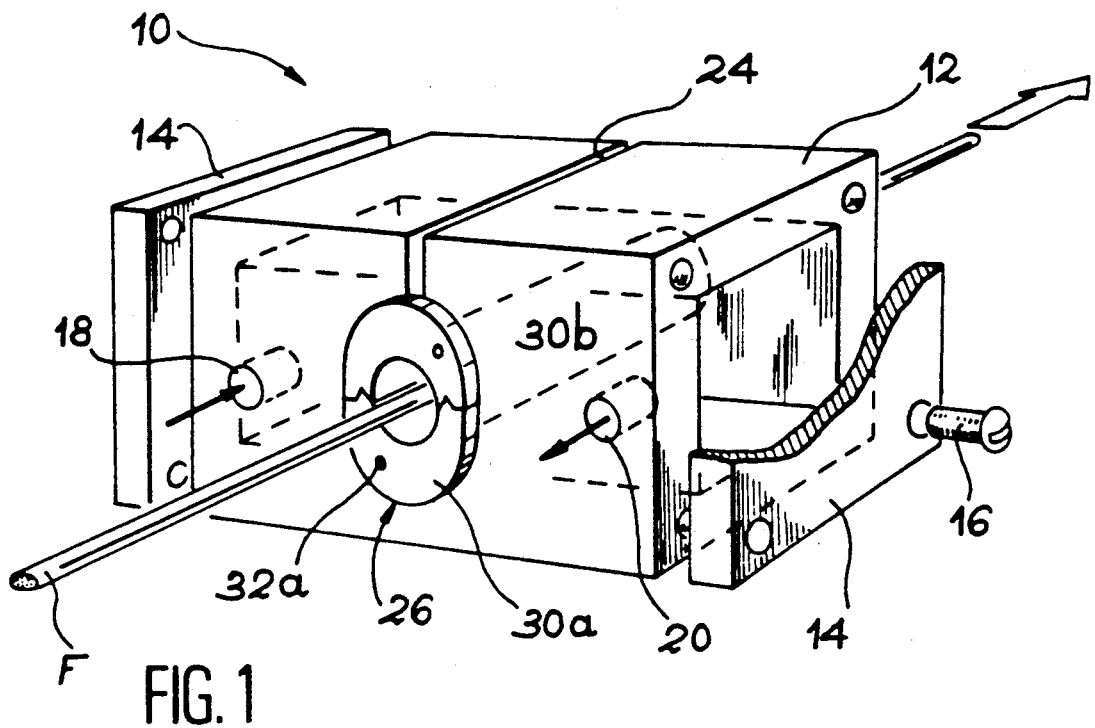

United States Patent [19]
Lahitte et al.

[11] Patent Number: 5,103,180
[45] Date of Patent: Apr. 7, 1992

[54] ULTRA-HIGH FREQUENCY CAVITY SUITABLE FOR THE MEASUREMENT OF ELECTROMAGNETIC CHARACTERISTICS OF A MOVING FILIFORM MATERIAL

[75] Inventors: Pierre Lahitte, Salaunes/St Medard en Jalles; Brigitte Prache, Bordeaux, both of France

[73] Assignee: Aerospatiale Societe Nationale Industrielle, France

[21] Appl. No.: 687,175

[22] Filed: Apr. 18, 1991

[30] Foreign Application Priority Data

Apr. 25, 1990 [FR] France .................. 90 05265

[51] Int. Cl.⁵ ............................................. G01N 22/00
[52] U.S. Cl. ................................. 324/636; 324/633; 324/629; 73/160
[58] Field of Search ............. 324/629, 632-636; 73/159, 160

[56] References Cited

U.S. PATENT DOCUMENTS 4,270,083 5/1981 Fitzky et al. .................. 324/636

FOREIGN PATENT DOCUMENTS 0372992 12/1989 European Pat. Off. .
2386033  3/1978 France .
2556470 12/1983 France .
2619217  8/1987 France .
63-145951 6/1988 Japan .

Primary Examiner—Jack B. Harvey
Attorney, Agent, or Firm—Hayes, Soloway, Hennessey & Hage

[57] ABSTRACT

In order to measure the electromagnetic characteristics of a moving filiform material without cutting the latter and without any risk of a liquid and/or solid pollution introduced by the material disturbing the measurements, an ultra-high frequency cavity (10) is proposed, whose wall (12) is traversed by two facing orifices, in which are placed the two open parts of a dismantlable tubular protective device (26). The slot (24) makes it possible to introduce the filiform material (F) in to the cavity. The device (26) isolates the filiform material from the latter and its production in two parts enables it to be put into place without cutting the material. The protective device (26) is replaced without stopping the measurements and without any pollution being able to enter the cavity.

7 Claims, 3 Drawing Sheets

ULTRA-HIGH FREQUENCY CAVITY SUITABLE FOR THE MEASUREMENT OF ELECTROMAGNETIC CHARACTERISTICS OF A MOVING FILIFORM MATERIAL

DESCRIPTION

The invention relates to an ultra-high frequency cavity resonator, resonant cavity or cavity for use in an industrial device making it possible to measure the electromagnetic characteristics such as the real and imaginary parts of the permittivity or permeability of a continuous and discontinuous, moving filiform material.

Such a cavity can in particular be used in combination with an ultra-high frequency source ensuring the excitation thereof, for measuring the electromagnetic characteristics of a polluting, composite filiform material, such as a wick impregnated with a viscous substance. The wick is then constituted by a plurality of fibres or fibrils made from a material such as carbon, which conducts electricity and is impregnated with a resin in the pasty or pregelled state. However, the cavity according to the invention can also be used for measuring the electromagnetic characteristics of a filiform material of a different nature, which may not be composite, not conductive and/or nonpolluting.

As is more particularly illustrated by FR-A-2 619 217, it is known to use an ultra-high frequency cavity, e.g. of the closed, cylindrical monomode type, excited in accordance with a given mode by an ultrahigh frequency source, in order to determine an electromagnetic quantity such as the complex permittivity of a filiform material travelling within the cavity. The filiform material then traverses the cavity by two facing orifices formed in the said wall, so as to be located in a region of the said cavity where the magnetic or electric field, as a function of the material to be tested, of a standing wave established in the cavity is at a maximum and substantially homogeneous.

The electromagnetic characteristics of the material are calculated as a function of the evolution of the resonance curve of the cavity. This curve represents the variations of the transmitted power or reflected power as a function of the resonant frequency, as a function of whether the cavity has one or two electrical measurement input-output facilities.

In the case where the filiform material is a polluting composite material, the measuring cavity can be polluted either by electricity-conducting fibrils producing short-circuits within the resonant cavity, or by a resin excess disturbing the calibration of the measuring system on flowing into the cavity. In both cases, the operating point of the cavity, i.e. the apex of the resonance curve, is displaced towards a lower frequency and power compared with the operating point of the cavity in the absence of any pollution. Consequently the measurements carried out are completely falsified.

Moreover, the ultra-high frequency cavity described in FR-A-2 619 217 is not appropriate for industrial use. Thus, then it is not possible to introduce a long filiform material into the cavity without cutting the wick, or to ensure the maintenance of the device without stopping the operation of the measuring system.

FR-A-2 386 033 and EP-A-0 011 185 describe an ultra-high frequency cavity making it possible to measure the electromagnetic characteristics of a sample, which must be accurately positioned within the cavity. For this purpose, the sample is placed in a cylindrical sample holder, which is put into place in a guide tube traversing the cavity. This guide tube cooperates with one of the cavity walls by a screw-nut system making it possible to ensure its longitudinal positioning.

However, the arrangement described in these two specifications is not suitable for carrying out measurements on a moving filiform material. In particular, it would no longer be possible with such a cavity to carry out measurements on a filiform material or carry out maintenance on the device without cutting the material and stopping the measurements. Moreover, in the case of a polluting filiform material, it would not be possible to replace the guide tube without dirtying the cavity.

The invention specifically relates to an ultra-high frequency cavity, whose original design makes it possible to carry out on an industrial scale measurements on a moving filiform material, even in the case where said material is of a polluting nature and without it being necessary at any time to cut the filiform material, without it being necessary to stop the measurements during maintenance operations and without any risk of polluting the cavity, even when these maintenance operations are carried out.

According to the invention this result is obtained by means of an ultra-high frequency cavity suitable for measuring the electromagnetic characteristics of a moving filiform material, incorporating a wall having two facing orifices permitting the passage of the filiform material, characterized in that the wall is also traversed by an open slot issuing into the two orifices and whose width allows the passage of the filiform material, a dismantlable tubular protective device traversing the cavity between the said orifices, said protective device having two open portions which can be juxtaposed edgewise around the filiform material.

In such a cavity, the open slot makes it possible to laterally introduce the filiform material into the orifices in order to bring it into its measuring position and without it being necessary to cut the said material. The tubular protective device protects the interior of the cavity against any pollution when the filiform material is a polluting material and its construction in two open parts permits its fitting and dismantling without it being necessary to cut the filiform material. Moreover, the tubular protective device can be introduced via one or other of the two orifices, in such a way that its replacement is ensured by a simple pushing action, the replacement device ejecting the spent device, so that even at this time the no pollution can penetrate the cavity.

In a preferred embodiment of the invention, each of the open portions of the protective device is shaped like a semi-cylinder of revolution.

Advantageously, in order to improve the protection of the cavity against pollution, the open portions of the protective device have complimentary lateral edges in the form of deflectors, which can be fitted into one another.

The open portions forming the tubular protective device can be fixed to one or other of the cavity walls by fixing members such as screws traversing the holes formed in a fixing collar or flange equipping one of the ends of said open portion.

In order to further improve the protection of the cavity against contamination during the replacement of the open portions of the tubular protective device, each of the said portions has, facing the end carrying the fixing flange, a terminal edge in the form of a deflector, which can be fitted into a complimentary terminal edge of a replacement open portions introduced in to the cavity by sliding.

A preferred embodiment of the invention is described in non-limitative manner hereinafter with reference to the attached drawings, wherein show:

FIG. 1 a perspective view showing an ultra-high frequency cavity designed, according to the invention, for carrying out measurements on a moving filiform material.

Figure 2:
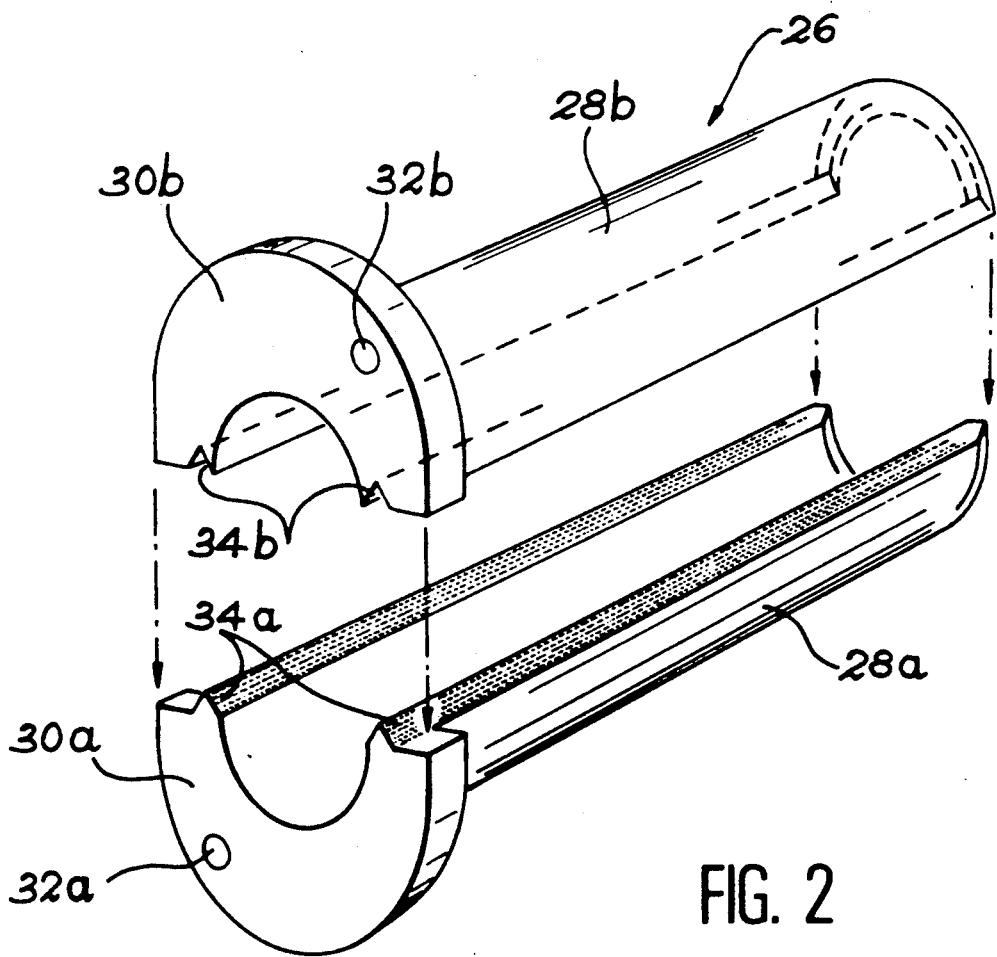

FIG. 2 a perspective view showing on a larger scale the two portions of a dismantlable tubular protecting device equipping the ultra-high frequency cavity of FIG. 1.

Figure 3A:
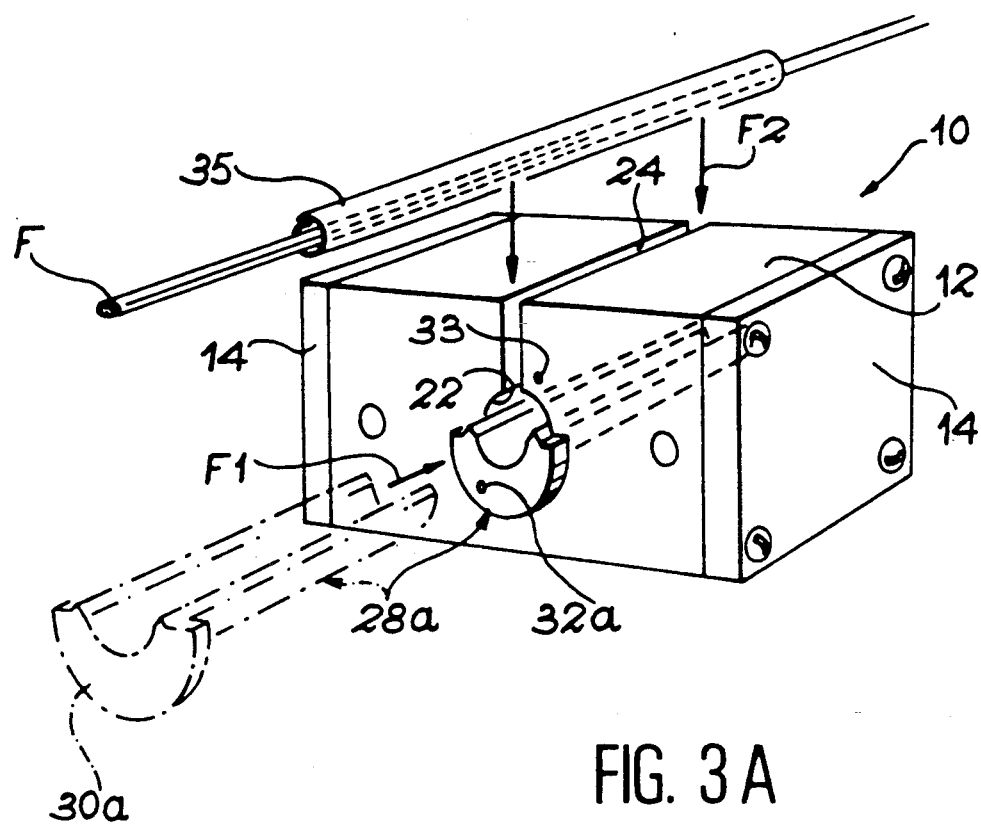
Figure 3B:
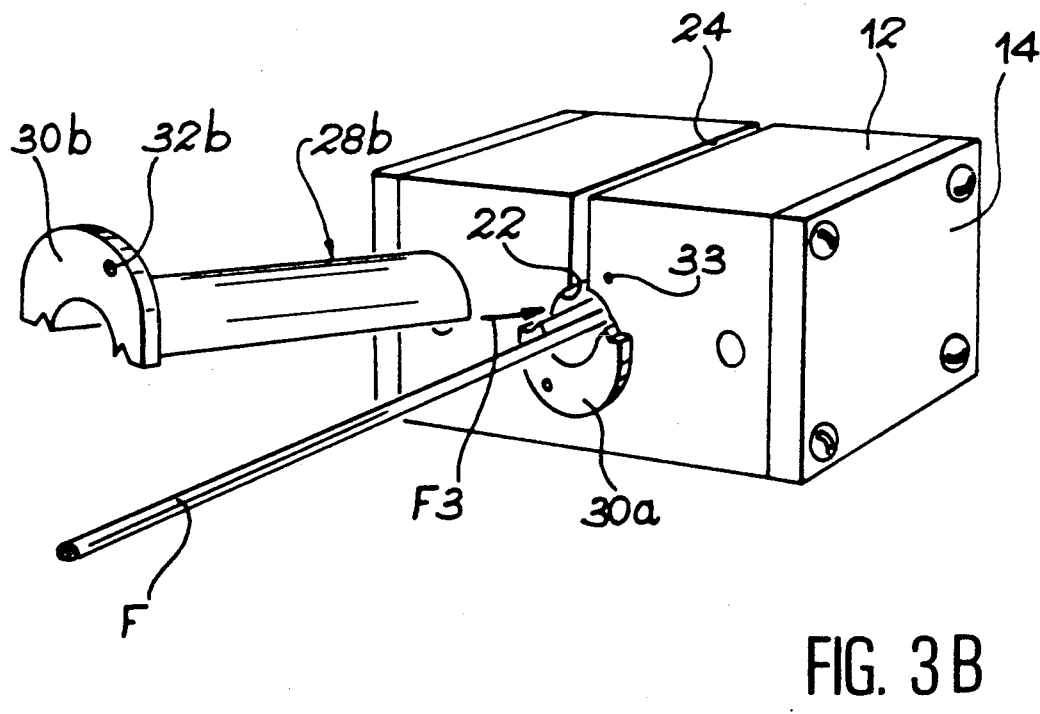

FIGS. 3A and 3B perspective views showing two successive stages on the operations making it possible to introduce a filiform material into the ultra-high frequency cavity according to the invention without cutting the said material.

Figure 4A:
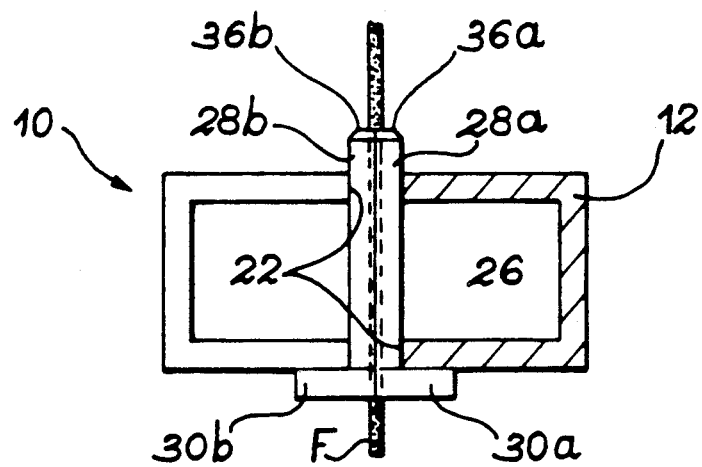
Figure 4B:
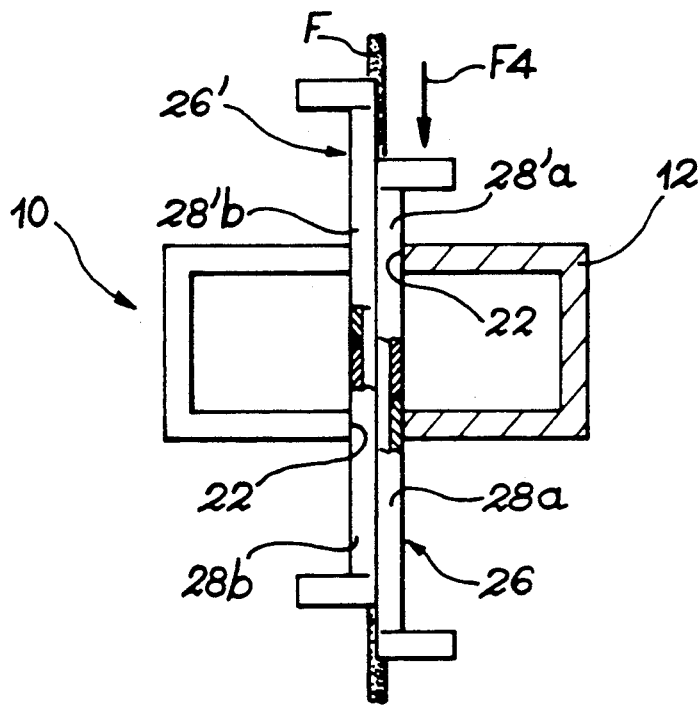
Figure 4C:
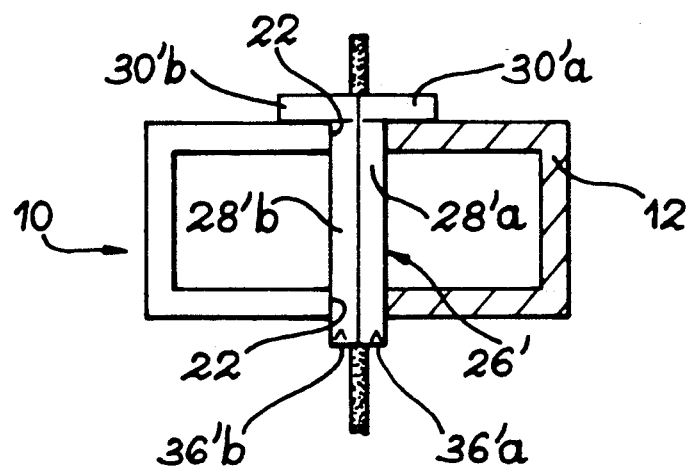

FIGS. 4A to 4C part sectional views very diagrammatically illustrating the replacement of the dismantlable tubular protective device of FIG. 2 with out interrupting the travel of the filiform material in the cavity and without any risk of introducing pollution into the latter.

In FIG. 1, reference numeral 10 designates in a general manner an ultrahigh frequency cavity defined by a wall 12 and e.g. made from Invar. The shape and dimensions of this resonant cavity are adapted to the particular measurements which it is wished to carry out and as a function of the general knowledge of the Expert. The diagrammatic representation of FIG. 1 must not be considered as being limitative in this respect.

In the embodiment shown, the ultra-high frequency cavity is a waveguide portion with a rectangular section, which is sealed at its ends by two short-circuits 14, also made from Invar and fixed to the wall 12, e.g. with the aid of screws 16.

In the embodiment shown, the wall 12 is traversed on one of its faces and in the vicinity of each of the connected walls 14 by an inlet 18 and an outlet 20. The inlet 18 is to be coupled to a not shown microwave source and the outlet 20 to a not shown detector by not shown transmission cables.

In order to permit the passage of the filiform material F on which the measurements are to be carried out, two of the parallel faces of the cavity wall 12, including that in which are formed inlet 18 and the outlet 20, are provided in their centre with circular orifices 22 (FIGS. 3 and 4) arranged coaxially and in facing manner. The diameter of these circular orifices 22, e.g. of approximately 6 mm, is chosen as a function of the size of the cavity and the dimensions of the filiform materials F on which the measurements are to be carried out, so that these materials can freely traverse a dismantlable tubular protective device 26 received in the orifices 22.

According to the invention, an open slot 24 traverses the wall 12 in accordance with a plain perpendicular to the longitudinal axis of the cavity and located equidistantly of the short-circuits 14, so as to issue into each of the two orifices 22 and to the exterior of the wall 12 on one of the faces of the latter oriented parallel to the axis common to the orifices 22. The position of the slot 24 is chosen in such a way as to interrupt the minimum of magnetic field H or electric field E lines for a device operating on the maximum of the electric field E or magnetic field H.

The open slot 24 has a uniform width, e.g. approximately 1.50 mm, chosen so as to permit the passage of the filiform material F in the direction of its smallest thickness (when it is a composite material wick, the filiform material normally has a substantially rectangular cross-section as shown in FIGS. 1, 3A and 3B). In order to ensure the rigidity of the measuring device, the face of the wall 12 opposite to the slot 24 is reinforced by a thickness increase.

According to another essential feature of the invention, a dismantlable tubular protective device 26 is placed within the circular orifices 22, so as to centrally traverse the ultra-high frequency cavity. Therefore this protective device 26 surrounds the filiform material F without ensuring the guidance, which is normally carried out on either side of the cavity by appropriate, but not shown means. Therefore the filiform material F is completely isolated from the interior of the cavity, so that the latter cannot be polluted when the filiform material is of a polluting nature.

The tubular protective device 26 is made from a material which disturbs to a minimum extent the measurements performed with the aid of the ultra-high frequency cavity 10. In addition, said material is advantageously chosen in such a way that there is a minimum adhesion of the polluting liquids or particles thereto. A material which simultaneously satisfies these two criteria is polytetrafluoroethylene, whose dielectric constant is low (2.01) and whose anti-adhesive properties are well known. Silica can also be used.

For example, the introduction of the protective device 26 into the cavity leads to its empty Q factor passing from 10,000 to 8,000, which is negligible compared with the variation of this factor between the empty cavity and the cavity loaded with an absorbent material. It is also possible to correct the variations caused by the protective device by using an appropriate software.

The tubular protective device 26 is more specifically shaped like a cylinder of revolution, whose uniform external diameter is equal to the internal diameter of the circular orifices 22, in such a way that the device can be introduced into the said orifices by sliding. The internal diameter of the device 26 is chosen as a function of the dimensions of the filiform material F, so as to prevent any rubbing of the latter against the wall of the device 26 without increasing the diameter of the latter to an exaggerated extent.

So that the tubular protective device 26 does not prevent the fitting and dismantling of the filiform material F through the slot 24, said device is formed by two complimentary open portions 28a and 28b, as is illustrated on a larger scale in FIG. 2. Each of these open portions 28a, 28b is shaped like a semi-cylinder of revolution, whose length preferably slightly exceeds the width of the cavity 10, increased by the thickness of the two faces of the wall 12 in the direction of the axis common to the two orifices 22. Each of the two portions 28a, 28b is produced in one piece, advantageously being obtained by machining from a different block, so as to reduce to the greatest possible extent the volume of material within the cavity (in order to optimise the measuring system). For example, for a $1.93 \times 10^5$ mm$^3$ cavity, said volume can be approximately 350 mm$^3$.

One of the ends of each of the open portions 28a, 28b of the protective device 26 has a semicircular shoulder or collar 30a, 30b facilitating handling and which is fixed to one or other of the two faces of the wall 12 in which are formed the orifices 22. This fixing is carried out by means of a not shown screw or some similar fixing member traversing a hole 32a,32b formed in each of the shoulders 30a,30b.

In the embodiment shown, when the two open portions 28a,28b of the protective device 26 are applied to one another, the two holes 32a,32b are at diametrically opposite locations with respect to the axis of the thus formed cylinder of revolution. However, these holes 32a,32b are displaced with respect to a plane of symmetry of each of the open portions 28a,28b. When the holes 32a,32b face tucked holes 33 (FIGS. 3A and 3B) formed in the corresponding face of the cavity wall 12, the junction plane of the two open portions 28a, 28b is oriented parallel to the two other faces of the wall 12.

In a first, not shown embodiment of the invention applied to the carrying out of measurements on a filiform material without mechanical pollution, the lateral or longitudinal edges of the open portions 28a,28b, which are applied to one another for forming the protective device 16, are planar edges contained in a junction plane passing through the axis common to these two open portions, which are then perfectly symmetrical.

In a second embodiment of the invention illustrated in the drawings, the lateral or longitudinal edges 34a and 34b of the two open portions 28a and 28b of the protective device 26 have complimentary shapes constituting deflectors when these edges 34a,34b are fitted into one another. Thus, in the embodiment of FIG. 2, the lateral edges 34a of the open portion 28a have a cross-section the shape of a projecting V, whereas the lateral edges 34b of the second open portion 28b have a cross-section in the form of a retracted V, which is complimentary to the projecting V formed by the edges 34a.

When the filiform material F is a mechanically polluting material having fibrils, this feature makes it possible to ensure that these fibrils are not attached between the lateral edges of the open portions 28a,28b so as to penetrate the cavity. It also contributes to a good relative positioning between these open portions.

As is illustrated by FIGS. 3A and 3B, the presence of the slot 24 and the construction in two portions 28a,28b of the protective device 26 make it possible, according to the invention, to introduce the filiform material F into the ultra-high frequency cavity 10 and to extract it therefrom at a random location of the length of said material without it being necessary to cut it or dismantle the cavity.

Thus, FIG. 3A shows that prior to the introduction of the filiform material F, the operator puts into place the open portion 28a positioned facing the slot 24 by making it slide successively into each of the orifices 22 (arrow F1). When the collar 30a of said portion 28a abuts against the corresponding face of the wall 12, it is fixed by a screw traversing the hole 32a, in the manner described hereinbefore.

The operator then introduces the filiform material F into the cavity by a relative movement between said material and the cavity symbolized by arrows F2 in FIG. 3A. During this relative movement, the filiform material traverses the slot 24 and is placed substantially in accordance with the axis of the semicylinder formed by the portion 20a, which has previously been put into place. Prior to this introduction a protective sleeve 35, e.g. in the form of a rolled up sheet of paper, is placed round that portion of the filiform material F which is traversed the slot 24 in order to prevent the sheets from entering the cavity. In addition, if necessary, the operator can manually orient the filiform material F, so that said material traverses the slot 24 in the direction of its smallest thickness.

The situation is then as illustrated in FIG. 3b and the second open portion 28b of the protective device 26 can in turn be introduced into the cavity by the same face as the first portion 28a already introduced. This introduction once again takes place by sliding through the orifices 22, the complimentary lateral edges 34a, 34b sliding on one another. This operation is illustrated by the arrow F3 in FIG. 3B. When the collar 30b of said second portion 28b abuts against the corresponding face of the case 12, it is in turn fixed by a screw passing through the hole 32b. The protective sleeve 35, which is not shown in FIG. 3b, is then removed by sliding along the axis common to the filiform material F and the protective device 24.

The desired measurement can then be carried out on the filiform material F by making the latter move continuously or discontinuously within the protective device constituted by the two complimentary portions 28a,28b and substantially without any contact with the said device. Any possible liquid or solid pollution resulting from the filiform material F is then confined in the protected device and cannot penetrate the cavity.

Preferably and contrary to what is shown in the drawings, the cavity 10 is oriented in such a way that the axis common to the orifices 22 and to the complimentary portions 28a, 28b of the device 26 is substantially vertical. This feature makes it possible to minimize friction between the filiform material and the protective device and to evacuate by gravity part of the polluting deposits which are deposited on the inner walls of said device.

Periodically, the internal walls can be cleaned without stopping the measurements, e.g. by introducing an air jet into the protective device. Moreover, one or both portions of the device can be dismantled so as to permit a more complete cleaning.

According to the invention, this dismantling of at least one of the two portions of the protective device consists of carrying out its replacement without interrupting the measurement and without at any instant breaking the material barrier constituted by said device. This replacement procedure will be described relative to FIGS. 4A to 4C.

FIG. 4A very diagrammatically shows the two open portions 28a,28b of a protective device 26 located in the orifices 22 positioned in facing manner in the wall 12 of an ultra-high frequency cavity 10. The collar 30a,30b of these two portions 28a,28b are fixed to one of the faces of the wall 12 having one of the orifices 22. When it is wished to replace the two portions 28a,28b of the protective device 26, e.g. for cleaning the same, the screws by which the collars 30a,30b are fixed to the corresponding face of the wall 12 are removed and through the orifice 22 formed in the opposite face of the wall 12 are introduced the two portions 28'a, 28'b of a replacement device 26'(Arrow F4). Advantageoulsy, this replacement takes place in the filiform material travel direction. During this replacement, the terminal edges 36'a, 36'b of each of the portions 28'a,28'b located opposite their collars 38'a, 38'b bear against the terminal edges 30a,30b of the two portions 28a, 28b to be replaced, so that the latter are moved by the portions 28'a, 28'b. However, as shown in FIG. 4B, at no time is the protection of the cavity with respect to possible pollution produced by the filiform material F, subject to an interruption.

When the collars or shoulders 30'a, 30'b of the two replacement portions 28'a, 28'b abut against the corresponding base of the wall 12, the two portions 28a, 28b of the protective device to be replaced are completely withdrawn from the cavity. The collars 30'a, 30'b are then fixed in the manner described hereinbefore to the said face of the wall 12.

It is important to observe that all the operations described hereinbefore with reference to FIGS. 4A, 4B and 4C are carried out without it being necessary to cut the filiform material F or even interrupt the movement or stop the measurements.

Like the lateral edges 34a,34b of the open portions 28a,28b, the terminal edges 36a,36b opposite the collars 30a,30b on each of the portions 28a,38b can either be planar edges oriented radially with respect to the axis of said portions, or non-planar edges.

In the latter case, illustrated in FIGS. 4A to 4C, the edges 36a,36b of the two portions 28a,28b of the protective device 26 to be replaced are complimentary of the edges 36'a,36'b of the two portions 28'a, 28'b of the replacement device 26'. When the terminal edges 36a,36b and 36'a,36'b bear against one another at the time of replacing device 26 by device 26', the non-planar complimentary surfaces 36a,36b and 36'a,36'b form deflectors, which prevent any passage within the cavity of mechanical pollution possibly introduced via the filiform material F. Thus, the cavity is completely protected against pollution, even at the time of replacing the protective device.

In the embodiment illustrated in FIGS. 4A to 4C, the terminal edge 36a,36b of each of the two portions 28a,28b of the device 26 has, in cross-section, the shape of a projecting V, whilst the terminal edge 36'a,36'b of each of the two portions 28'a,28'b of the device 26' has, in cross-section, the shape of a retracted V complimentary to the projecting V. Obviously, when the portions 28'a,28'b of the device 26' are in turn replaced, use will again be made of the portions 28a,28b, whose terminal edges form projecting V's in cross-section.

The above description has revealed that the ultra-high frequency cavity according to the invention is perfectly suitable for industrial use, because measurements can be carried out without it being necessary at any time to cut the travelling filiform material. Moreover, the cavity can be maintained without interrupting the measurements and the quality of the latter can be preserved no matter what type of filiform material is subject to such measurements, particularly when said material is of a polluting nature. However, the invention is obviously not limited to the embodiment described in exemplified manner hereinbefore and covers all variants thereof.

It is firstly pointed out that the characteristics of the invention can be transposed to ultra-high frequency cavities of all shapes and sizes, said characteristics being determined as a function of the nature of the measurements to be carried out.

It is also pointed out that the ultra-high frequency cavity according to the invention can be used for carrying out measurements on a random filiform material, no matter whether or not it is of a polluting nature and independently of the fact that of whether said material is moved continuously or discontinuously. Thus, the invention can be used for measuring deposits on textile filaments or on fibres during the production thereof, or for carrying out measurements and size checks on a homogeneous material such as an optical fibre.

In addition, it is clear that the shape of the open portions constituting the dismantlable tubular protective device can differ from those described and said two portions can in particular by asymmetrical and need not be shaped like semicylinders of revolution. The two portions of the protecting device can also be fixed differently without passing beyond the scope of the invention. It has also been seen that the shapes of the lateral edges and the terminal edges of said open portions can be planar or non-planar as a function of the type of filiform material on which the measurements are performed. Finally, the material constituting the protective device can be of any nature having low losses and the volume of the device present in the cavity is not critical.

We claim:

1. Ultra-high frequency cavity suitable for measuring the electromagnetic characteristics of a moving filiform material, incorporating a wall having two facing orifices permitting the passage of the filiform material, characterized in that the wall is also traversed by an open slot issuing into the two orifices and whose width allows the passage of the filiform material, a dismantlable tubular protective device traversing the cavity between the said orifices, said protective device having two open portions which can be juxtaposed edgewise around the filiform material.

2. Ultra-high frequency cavity according to claim 1, wherein each of the said open portions is shaped like a semi-cylinder of revolution.

3. Ultra-high frequency cavity according to claim 1, wherein said open portions have complimentary lateral edges in the form of deflectors, which can be fitted into one another.

4. Ultra-high frequency cavity according to claim 1, wherein each of the said open portions has at one of its ends a fixing collar perforated by at least one hole for the passage of a member for fixing the collar to the cavity wall.

5. Ultra-high frequency cavity according to claim 4, wherein, opposite to its end carrying the fixing collar, each of the said open portions has a terminal edge in the form of a deflector which can be fitted into a complimentary terminal edge of a replacement open portion introduced into the said cavity by sliding.

6. Ultra-high frequency cavity according to claim 1, wherein the open slot is located in a plane perpendicular to the longitudinal axis of the cavity and equidistantly of the ends of the latter.

7. Ultra-high frequency cavity according to claim 1, wherein the axis common to the said orifices is substantially vertical.

* * * * *